United States Patent [19]
Alper et al.

[11] Patent Number: 4,681,707
[45] Date of Patent: Jul. 21, 1987

[54] PROCESS FOR THE PRODUCTION OF CARBOXYLIC ACID ESTERS AND/OR CARBOXYLIC ACIDS

[75] Inventors: Howard Alper, Ottawa, Canada; Bertrand Despeyroux, Hanau, Fed. Rep. of Germany; David J. H. Smith, Camberley, United Kingdom; James B. Woell, Ottawa, Canada

[73] Assignee: The British Petroleum Company p.l.c., London, England

[21] Appl. No.: 606,812

[22] PCT Filed: Sep. 28, 1983

[86] PCT No.: PCT/GB83/00240

§ 371 Date: Apr. 23, 1984

§ 102(e) Date: Apr. 23, 1984

[87] PCT Pub. No.: WO84/01376

PCT Pub. Date: Apr. 12, 1984

[30] Foreign Application Priority Data

Sep. 30, 1982 [GB] United Kingdom ................. 8227972
Feb. 24, 1983 [GB] United Kingdom ................. 8305182

[51] Int. Cl.[4] ............................................. C07C 67/38
[52] U.S. Cl. ................. 260/410.9 R; 560/105; 560/114; 560/204; 560/206; 560/232; 560/233; 560/97; 562/406; 562/497; 562/522
[58] Field of Search ................. 260/410.9 R; 560/206, 560/233, 97, 114, 105, 204, 232; 562/522, 406, 497

[56] References Cited

U.S. PATENT DOCUMENTS

| 3,023,237 | 2/1962  | Reppe ............................ 562/522 |
| 3,065,242 | 11/1962 | Alderson et al. ................ 562/522 |
| 3,397,225 | 8/1968  | Fenton ............................ 560/207 |
| 3,397,226 | 8/1968  | Fenton ............................ 560/232 |
| 3,501,518 | 3/1970  | Kutepow ......................... 560/233 |
| 3,530,168 | 9/1970  | Biale .............................. 560/207 |
| 3,579,568 | 5/1971  | Heck et al. ..................... 560/233 |
| 3,717,670 | 2/1973  | Schultz .......................... 562/522 |
| 3,755,421 | 8/1973  | Fenton ............................ 560/233 |
| 3,952,034 | 4/1976  | Thompson et al. ............. 562/522 |
| 4,234,740 | 11/1980 | Umemura et al. .............. 560/114 |
| 4,257,973 | 3/1981  | Mrowca .......................... 560/233 |
| 4,354,978 | 10/1982 | Frampton ....................... 560/233 |
| 4,414,409 | 11/1983 | Waller ............................. 560/233 |

FOREIGN PATENT DOCUMENTS

| 2630268  | 1/1977 | Fed. Rep. of Germany . |
| 2328689  | 5/1977 | France . |
| 41-12215 | 7/1966 | Japan .................. 560/233 |
| 2009733  | 6/1979 | United Kingdom . |

OTHER PUBLICATIONS

Falbe, "Carbon Monoxide in Organic Synthesis", p. 78-122 (1970).
Yoneda, Bull. Chem. Soc. Jpn., pp. 2347-2353, (1978), vol. 51.

Primary Examiner—Michael L. Shippen
Attorney, Agent, or Firm—Brooks Haidt Haffner & Delahunty

[57] ABSTRACT

Carboxylic acid esters are produced by reacting an unsaturated hydrocarbon, for example an olefin or an alkyne, with carbon monoxide and an alcohol in the presence of a protonic acid and as catalyst (a) at least one of the metals palladium, rhodium, ruthenium, iridium and cobalt, and (b) copper. In a modification of the invention carboxylic acids are produced by omitting the alcohol reactant and replacing it with water in an amount up to 8 mole equivalents based on the unsaturated hydrocarbon and a solvent other than an alochol, for example tetrahydrofuran.

11 Claims, No Drawings

PROCESS FOR THE PRODUCTION OF CARBOXYLIC ACID ESTERS AND/OR CARBOXYLIC ACIDS

The present invention relates in general to a process for the production of carboxlyic acid esters and/or carboxylic acids and in particular to a process for the production of carboxylic acid esters and/or carboxylic acids by the catalysed reaction of an unsaturated hydrocarbon, carbon monoxide and either water or an alcohol, optionally in the presence of oxygen.

Processes for the production of esters by reacting an olefin with carbon monoxide and an alcohol in the presence of a catalyst and in the presence or absence of oxygen are known. Representative of the published art are U.S. Pat. No. 4,303,589, Belgian Pat. No. 877770, Japanese Patent Publication No. 53040709 and U.S. Pat. No. 3,780,074.

U.S. Pat. No. 4,303,589 (Monsanto) describes a process for the production of carboxylate esters by (a) reacting internal olefins with carbon monoxide and an alcohol at 170° to 200° C. and 1200–1800 psig in the presence of a cobalt catalyst and a pyridine promoter, (b) diluting the reaction mixture with a large amount of hydrocarbon to cause phase separation, (c) separating the ester from the other phase, which contains more than 90% of the cobalt catalyst and (d) recycling the catalyst to step (a).

Belgian Pat. No. 877770 describes the production of polycarboxylic esters by reacting an olefin containing at least two conjugated double bonds with carbon monoxide and an alcohol in the presence of a base and a palladium/copper catalyst.

Japanese Patent Publication No. 5 3040 709 describes the production of dicarboxylic acid diesters by reacting an olefin, carbon monoxide, oxygen and an alcohol in the presence of a catalyst containing (a) a palladium group metal or a compound thereof, (b) a copper salt and (c) a tertiary amine.

Finally, U.S. Pat. No. 3,780,074 describes the production of alkadienoic acid esters by reacting a 4–12 carbon acyclic conjugated aliphatic diolefin with a 1 to 20 carbon monohydroxy alcohol and carbon monoxide in the presence of zero valent palladium and a phosphine activator at 80° to 160° C. in the absence of oxygen.

Methods are also known for the hydroesterification of acetylene to produce isomeric esters. For example, G. P. Chiusli et al report in Chem. Ind., 977, (1968) the reaction of acetylene with carbon monoxide in the presence of 4% oxygen and thiourea and a palladium (II) chloride catalyst. A disadvantage of this process is that the selectivity to isomeric esters (cis and trans-diesters) is considerably reduced by the accompanying formation of polymeric materials and isomeric muconate esters.

We have now found that carboxylic acid esters and/or carboxylic acids can be produced by reacting an unsaturated hydrocarbon with carbon monoxide and either water or an alcohol in the presence of a protonic acid and as catalyst (a) at least one of the metals palladium, rhodium, ruthenium, iridium and cobalt, and (b) copper, both in the presence and the absence of oxygen. In contrast with the majority of prior art processes which utilize a base as an essential reactant, the process of the present invention utilises an acid. The process of the invention in contrast with prior art processes can be operated under relatively mild conditions and exhibits a high regiospecificity to desirable products.

Accordingly, the present invention in one aspect provides a process for the production of a carboxylic acid ester which process comprises reacting an unsaturated hydrocarbon with carbon monoxide and an alcohol in the presence of a protonic acid and as catalyst (a) at least one of the metals palladium, rhodium, ruthenium, iridium and cobalt, and (b) copper.

The unsaturated hydrocarbon may suitably be an olfein. The olefin may suitably be an acyclic olefin containing from 2 to 30 carbon atoms per molecule or a cyclic olefin containing from 5 to 30 carbon atoms per molecule. The olefin may have either 1, 2 or 3 olefinic carbon-carbon double bonds per molecule, which double bonds may be internal or terminal and may be conjugated or non-conjugated in olefins containing a plurality of carbon-carbon double bonds. Suitable olefins may be represented by the general formula $RCH=CHR^1$ wherein R and $R^1$ are independently either hydrogen, alkyl, alkenyl, alkadienyl, cycloalkyl, aryl, alkaryl, cycloalkenyl or cycloalkadienyl groups, or R and $R^1$ taken together form a cyclic system. Examples of suitable mono-olefins include propylene, 1-butene, 2-butene, 1-pentene, 2-pentene, 1-hexene, 2-hexene, 3-hexene, 1-octene, 1-decene, cyclododecene, 2-methyl-1-undecene, styrene, 4-methylstyrene, 4-isopropylstyrene, and the like. Examples of suitable diolefins include 1,3-butadiene, 1,3-pentadiene, 1,5-hexadiene, 4-vinyl cyclohexene, 1,7-octadiene, 1,9-decadiene and the like. Alternatively the diolefin may be allene or an allene homologue, for example dimethyl allene. Examples of suitable triolefins include 1,5,9-cyclododecatriene, cycloheptatriene and the like. Mixtures of olefins may also be employed. Terminal mono-olefins react to give branched chain esters. Internal mono-olefins, for example 2-decene and 4-methyl-2-pentene react exclusively at the 2-position, the cis-isomer being more reactive than the trans-isomer.

Alternatively, the unsaturated hydrocarbon may be an alkyne. The alkyne may be either a terminal or an internal alkyne. Suitable terminal alkynes include acetylene, 1-pentyne, 1-hexyne, 1-octyne, benzylacetylene, cyclohexylacetylene and 3-methyl-1-pentyne. Suitable internal alkynes include 2-heptyne, 2-nonyne, 4-methyl-2-pentyne and 2,9-dimethyl-5-decyne. Typically, using acetylene as the unsaturated hydrocarbon the product principally comprises dimethyl maleate together with a minor proportion of dimethyl furmarate. Generally, terminal alkynes give the cis-diester as the principal product and the trans-diester as a by-product. Internal alkynes on the other hand generally give monoesters, not diesters, and furthermore the monoesters tend to be of cis stereochemistry.

The carbon monoxide may be provided by any suitable source. The carbon monoxide pressure may suitably be the autogenous pressure at the reaction temperature employed. Alternatively, elevated pressures, suitably in the range from 2 to 250 psig above the autogenous pressure at the reaction temperature may be employed.

As regards the alcohol reactant, monohydric and polyhydric alcohols may be employed. Suitable alcohols may be represented by the formula $R_2CHOH$ wherein R is independently hydrogen, alkyl, aryl or hydroxyalkyl, or the two groups R together form a ring. Suitably the alcohol is an alkanol. Examples of suitable alcohols include methanol, ethanol, propanols, butanols, pentanols, hexanols, for example 2-ethylhexanol, benzyl alcohol and 1,4-butanediol. The amount of alcohol employed may suitably be at least the stoichiometric amount required to react with the unsaturated hydrocarbon. It is preferred, however, to employ a substantial excess of alcohol over the stoichiometric amount, the alcohol then performing the dual role of reactant and diluent for the reaction.

The protonic acid may be either a mineral acid, preferably hydrochloric acid or sulphuric acid, or an organic acid which may suitably be a carboxylic acid.

With regard to the catalyst, one or more of the metals palladium, rhodium, ruthenium, iridium and cobalt is employed as component (a). The metal(s) may be in the form of the elemental metal(s), such as a finely divided powder, or in the form of a compound of the metal(s). Suitable compounds of the metal(s) include the chlorides, iodides, acetates and nitrates, preferably the chlorides. Preferably the metal is palladium, suitably in the form of palladium (11) chloride.

Copper, which constitutes component (b) of the catalyst may suitably be added as a cuprous or a cupric compound or as a mixture thereof. A wide variety of copper compounds may be used in the process of the invention. Examples of suitable copper compounds include copper (I) acetate, copper (11) acetylacetonate, copper (I) bromide, copper (I) chloride, copper (11) chloride, copper (I) iodide, copper (11) nitrate, and the like.

As regards the ratios of the catalyst components, the molar ratio of copper components (b) to metal(s) component (a) may suitably be in the range from 1:1 to 200:1, preferably from 2:1 to 60:1.

The molar ratio of unsaturated hydrocarbon to the metal(s) component (a) may suitably be in the range from 5:1 to 1000:1, preferably from 10:1 to 250:1.

Oxygen may be present or absent. However, it is preferred to operate in the presence of oxygen because by doing so the product yields can be improved. Oxygen may be supplied to the reaction either as essentially pure oxygen or admixed with other gases which are substantially inert under the reaction conditions. Air may conveniently be used as the source of oxygen. The oxygen pressure may suitably be the autogenous pressure at the reaction temperature employed. Alternatively elevated pressures may be employed if desired.

A supplemental solvent may be employed if desired. The particular solvent employed may form a single phase with the alcohol reactant. Alternatively a solvent which is capable of forming a second liquid phase may be employed. The particular solvent employed should be inert under the reaction conditions. Suitable solvents which form a single phase with the alcohol reactant include oxygenated hydrocarbons, for example tetrahydrofuran. Suitable solvents capable of forming a second liquid phase include aliphatic hydrocarbons, cycloaliphatic hydrocarbons, aromatic hydrocarbons, alkyl-substituted aromatic hydrocarbons or halogenated aliphatic or aromatic hydrocarbons. Examples of suitable solvents capable of forming a second liquid phase include benzene, toluene, hexane, cyclohexane, chlorobenzene, bromobenzene, a xylene, dichloromethane, chloroform and 1,2-dichloroethane. It will be appreciated by those skilled in the art that the organic solvent should be chosen having regard to the difference in boiling points between the products of the reaction and the solvent so as to facilitate separation of the reaction mixture into its individual components. The amount of supplemental solvent based on the olefin reactant may vary over a wide range, suitably from 20 to 0.2, preferably from 5 to 1, volumes of supplemental solvent per volume of olefin reactant.

If, in a modification of the invention, the alcohol reactant is replaced by water, provided that the amount of water is less than 8 mole equivalents based on the unsaturated hydrocarbon reactant and a solvent other than an alcohol is employed, then instead of carboxylic acid ester, there is formed the corresponding carboxylic acid.

Preferably the amount of water employed is less than 5, even more preferably about 1 mole equivalent based on the unsaturated hydrocarbon reactant.

Any suitable solvent other than an alcohol may be employed. Suitable solvents include ethers and hydrocarbons, for example paraffinic and aromatic hydrocarbons. Preferably the solvent is an ether. Examples of suitable ethers include tetrahydrofuran, dioxan, glymes and the crown ethers, of which tetrahydrofuran is preferred.

The process may suitably be operated at ambient temperature, though elevated temperatures, for example in the range 20° to 150° C. or even higher may be employed. The reaction time may vary over a wide range, suitably from about 30 minutes to 8 hours, though longer reaction times may be employed if desired.

The process may be carried out batchwise or continuously, preferably continuously.

The invention will now be described in greater detail by reference to the following Examples.

PROCESS OPERATED IN THE PRESENCE OF OXYGEN

EXAMPLE 1

Palladium (11) chloride (0.1 g; 0.56 mmol) was added to methanol (50 ml) through which was bubbled carbon monoxide (1 atmosphere). After 1 minute conc. hydrochloric acid (0.5 ml) was added. When the solution turned yellow (indicating that the palladium chloride had dissolved), copper (11) chloride (0.5 g; 3.7 mmol) was added and oxygen (1 atmosphere) was bubbled through the solution in addition to the carbon monoxide. 1-Decene (6 mmol) was then added and the reaction mixture was stirred for 4 hours at 25° C. After 2 hours a further 0.5 ml conc. hydrochloric acid was added.

The reaction product was then extracted with hexane and the hexane evaporated to give a pure product which was identified as methyl 2-methyl decanoate. The ester was obtained in 100% yield based on olefin reactant.

EXAMPLE 2

Example 1 was repeated except that 1-decene was replaced by 1,7-octadiene.

EXAMPLE 3

Example 1 was repeated except that 1-decene was replaced by 1,9-decadiene and the reaction time was reduced to 3 hours.

EXAMPLE 4

Example 1 was repeated except that 1-decene was replaced by cyclododecene.

EXAMPLE 5

Example 1 was repeated except that 1-decene was replaced by propene.

EXAMPLE 6

Example 1 was repeated except that 1-decene was replaced by 2-methyl-1-undecene and the product was separated by distillation after extraction with hexane.

EXAMPLE 7

Example 6 was repeated except that 2-methyl-1-undecene was replaced by 4-methylstyrene.

The results of Examples 2 to 7 together with those of Example 1 are given in Table 1.

EXAMPLE 8

Example 1 was repeated except that the conc. hydrochloric acid was replaced by conc. sulphuric acid (0.33 g).

Methyl 2-methyl decanoate was obtained in 92% yield.

EXAMPLE 9

The procedure of Example 1 was repeated except that instead of methanol there was used 1,4-butane diol (0.7 g) and tetrahydrofuran (30 ml) was used as a supplemental solvent. The amounts of other reactants were as follows:
palladium (II) chloride = 0.7 mmol
copper (II) chloride = 6 mmol
conc. hydrochloric acid = 0.1 ml
1-decene = 1.09 g
The carbon monoxide/oxygen was bubbled through the mixture for 16 hours.

After distillation of the crude product, the pure monoester of formula

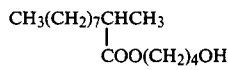

was obtained in 50% yield.

EXAMPLE 10

Palladium (11) chloride (0.1 g; 0.56 mmol) was added to methanol (50 ml) through which was bubbled carbon monoxide (1 atmosphere). After 1 minute conc. hydrochloric acid (0.5 ml) was added. When the solution turned yellow (indicating that the palladium chloride had dissolved), copper (11) chloride (0.5 g; 3.7 mmol) was added and oxygen (1 atmosphere) was bubbled through the solution in addition to the carbon monoxide. Acetylene (6 mmol) was then bubbled through the solution for 4 hours at 25° C. After 2 hours a further 0.5 ml conc. hydrochloric acid was added.

The reaction product was then extracted with hexane and the hexane evaporated. Analysis of the product give dimethyl maleate (86% yield) and dimethyl fumarate (14% yield).

EXAMPLE 11

The procedure of Example 1 was repeated except that acetylene was replaced by 1-pentyne. Cis- and trans-$C_3H_7C(COOCH_3)$=$CHCOOCH_3$ were obtained in 72 and 25% yield respectively.

EXAMPLE 12

The procedure of Example 10 was repeated except that acetylene was replaced by 1-hexyne. Cis- and trans-$C_4H_9C(COOCH_3)$=$CHCOOCH_3$ were obtained in 76 and 24% yield respectively.

EXAMPLE 13

The procedure of Example 10 was repeated except that acetylene was replaced by 1-octyne. Cis- and trans-$C_6H_{13}C(COOCH_3)$=$CHCOOCH_3$ were obtained in 80 and 20% respectively.

EXAMPLE 14

The procedure of Example 10 was repeated except that acetylene was replaced by benzyl acetylene. Cis- and trans-$PhCH_2CH_2C(COOCH_3)$=$CHCOOCH_3$ were obtained in 74 and 26% yield respectively

EXAMPLE 15

The procedure of Example 10 was repeated except that acetylene was replaced by cyclohexylacetylene. Cis- and trans-$C_6H_{11}C(COOCH_3)$=$CHCOOCH_3$ were obtained in 85 and 15% yield respectively.

EXAMPLE 16

The procedure of Example 10 was repeated except that acetylene was replaced by 3-methyl-1-pentyne. Cis- and trans-$C_2H_5CH(CH_3)C(COOCH_3)$=$CHCOOCH_3$ were obtained in 84 and 16% yield respectively.

EXAMPLE 17

The procedure of Example 10 was repeated except that acetylene was replaced by 2-heptyne. $CH_3(CH_2)_3CH$=$C(CH_3)COOCH_3$ and an ether were obtained in 90 and 10% yield respectively.

EXAMPLE 18

The procedure of Example 10 was repeated except that acetylene was replaced by 2-nonyne.
$CH_3(CH_2)_5CH$=$C(CH_3)COOCH_3$ and an ether were obtained in a ratio of 60 and 40% yield respectively.

EXAMPLE 19

The procedure of Example 10 was repeated except that acetylene was replaced by 4-methyl-2-pentyne. $(CH_3)_2CHCH$=$C(CH_3)COOCH_3$ and an ether were obtained in 75 and 25% yield respectively.

EXAMPLE 20

The procedure of Example 10 was repeated except that acetylene was replaced by 2,9-dimethyl-5-decyne. Cis-$(CH_3)_2CHCH_2CH_2CH$=$C(CH_2CH_2CH[CH_3]_2)COOCH_3$ and an ether were obtained in 70 and 30% yield respectively.

EXAMPLE 21

Example 15 was repeated except that methanol was replaced by ethanol. Cis- and trans-$C_6H_{11}C(COOC_2H_5)$=$CHCOOC_2H_5$ were obtained in 86 and 13% yield respectively.

EXAMPLE 22

Example 17 was repeated except that n-propyl alcohol was used in place of methanol.
Cis-$CH_3(CH_2)_3CH$=$C(CH_3)COOC_3H_7$ was obtained in 76% yield.

In Examples 10 to 22 the % yields are based on reactant alkyne.

EXAMPLE 23

Carbon monoxide was bubbled through a solution containing tetrahydrofuran (30 ml) and water (1 ml). Palladium (II) chloride (0.140 g, 0.78 mmol) was added, followed by concentrated hydrochloric acid (1.0 ml), copper (II) chloride (0.84 g, 6.24 mmol), and then oxygen was bubbled through the mixture. 1-Decene (7.8 mmol) was added and the reaction mixture was stirred at room temperature for 4 hours.

The product was worked-up by adding distilled water (50 ml) and extracting three times with hexane (in total 250 ml). The extract was dried using magnesium sulphate and then concentrated. Further purification was carried out by dissolving the acid in 1M NaOH, extracting with ether, acidifying, and extracting again with ether.

2-Methyldecanoic acid was obtained in 100% yield.

EXAMPLE 24

The procedure of Example 23 was repeated except that 1-decene was replaced by 1-octene and the reaction time was increased to 18 hours.

2-Methyloctanoic acid was obtained in 92% yield.

EXAMPLE 25

The procedure of Example 23 was repeated except that 1-decene was replaced by vinylcyclohexene.

$C_6H_{11}CH(CH_3)COOH$ was obtained in 53% yield.

EXAMPLE 26

The procedure of Example 25 was repeated except that the reaction time was increased to 18 hours.

$C_6H_{11}CH(CH_3)COOH$ was obtained in 89% yield.

EXAMPLE 27

The procedure of Example 23 was repeated except that 1-decene was replaced by 1,7-octadiene and the reaction time was increased to 18 hours.

$HOCOCH(CH_3)(CH_2)_4CH(CH_3)COOH$ was obtained in 93% yield.

EXAMPLE 28

The procedure of Example 23 was repeated except that 1-decene was replaced by 1,9-decadiene and the reaction time was increased to 18 hours.

$HOCOCH(CH_3)(CH_2)_6CH(CH_3)COOH$ was obtained in 100% yield.

EXAMPLE 29

The procedure of Example 23 was repeated except that 1-decene was replaced by cis-2-decene.

$CH_3(CH_2)_7CH(CH_3)COOH$ was obtained in 59% yield.

EXAMPLE 30

The procedure of Example 23 was repeated except that 1-decene was replaced by trans-2-decene.

$CH_3(CH_2)_7CH(CH_3)COOH$ was obtained in 30% yield.

EXAMPLE 31

The procedure of Example 30 was repeated except that the time was increased to 18 hours.

$CH_3(CH_2)_7CH(CH_3)COOH$ was obtained in 77% yield.

EXAMPLE 32

The procedure of Example 23 was repeated except that cyclododecene was used instead of 1-decene. The yield of cyclododecanecarboxylic acid was 64%.

EXAMPLE 33

The procedure of Example 23 was repeated except that cis-4-methyl-2-pentene was used instead of 1-decene. The yield of 2,4-dimethylpentanoic acid was 84%.

EXAMPLE 34

The procedure of Example 23 was repeated except that trans-4-methyl-2-pentene was used instead of 1-decene. The yield of 2,4-dimethylpentanoic acid was 64%.

EXAMPLE 35

The procedure of Example 23 was used except that instead of 1-decene there was used 1,7-octadiene (1.15 ml; 7.8 mmol). The amounts of the other reactants were as follows:
Tetrahydrofuran = 30 ml
Palladium (II) chloride = 0.130 g (0.7 mmol)
Conc. hydrochloric acid = 0.1 ml
Copper (II) chloride = 6 mmol.
Water = 0.14 ml (7.8 mmole)
Carbon monoxide/oxygen was bubbled through the mixture for 16 hours.

An 80% mixture of the monoacids of formula:

$CH_3CH(COOH)(CH_2)_4CH=CH_2$ and $CH_3CH(COOH)(CH_2)_3CH=CH_2CH_3$ were obtained.

PROCESS OPERATED IN THE ABSENCE OF OXYGEN

EXAMPLE 36

Palladium (11) chloride (0.1 g; 0.56 mmol) was added to methanol (50 ml) through which was bubbled carbon monoxide (1 atmosphere). After 1 m conc. hydrochloric acid (1.0 ml) was added. The solution turned yellow. 1-Decene (6 mmol) was added and the reaction mixture was stirred at room temperature. When the reaction mixture turned green, a small amount of copper (11) chloride was added [1:1 ratio overall of palladium (11) chloride to copper (11) chloride]. This operation was repeated as long as the solution turned green. Eventually the solution remained yellow, at which point it was extracted with hexane. The hexane was then evaporated to give methyl 2-methyl decanoate in 100% yield.

TABLE 1

| EXAMPLE | OLEFIN | PRODUCT | YIELD (%) |
|---|---|---|---|
| 1 | 1-decene |  | 100 |
| 2 | 1,7-octadiene |  | 100 |
| 3 | 1,9-decadiene | $CH_3OOCCH(CH_2)_6CHCOOCH_3$ with $CH_3$ branches | 70 |

TABLE 1-continued

| EXAMPLE | OLEFIN | PRODUCT | YIELD (%) |
|---|---|---|---|
| 4 | cyclododecene | methyl cyclododecane carboxylate | 85 |
| 5 | propene | $(CH_3)_2CHCOOCH_3$ | 100* |
| 6 | 2-methyl-1-undecene | $C_9H_{19}C(CH_3)_2COOCH_3$ | 63 |
|   |   | $C_9H_{19}C(CH_3)_2OCH_3$ | 18 |
|   |   | Internal olefin | 8 |
| 7 | 4-methylstyrene | $4\text{-}CH_3C_6H_4\underset{\underset{CH_3}{\mid}}{C}HCOOCH_3$ | 90 |
|   |   | $4\text{-}CH_3C_6H_4\underset{\underset{CH_3}{\mid}}{C}HOCH_3$ | 8 |
|   |   | Internal olefin | 2 |

*The yield is approximate since the exact weight of propene was not determined. No $CH_3CH_2CH_2COOCH_3$ was isolated.

EXAMPLE 37

Example 36 was repeated except that 1-decene was replaced by 1-pentene.

EXAMPLE 38

Example 36 was repeated except that 1-decene was replaced by 2-methyl-1-undecene and the product was separated by distillation after extraction with hexane.

EXAMPLE 39

Example 36 was repeated except that 1-decene was replaced by 4-methylstyrene and the product was separated by distillation after extraction with hexane.

The results of Examples 36 to 39, together with those for Example 36, are given in Table 2.

In Examples 23 to 39 the % yields are based on reactant olefin.

TABLE 2

| EXAMPLE | OLEFIN | PRODUCT | YIELD (%) |
|---|---|---|---|
| 36 | 1-decene | $C_8H_{17}\underset{\underset{CH_3}{\mid}}{C}HCOOCH_3$ | 100 |
| 37 | 1-pentene | $C_3H_7\underset{\underset{CH_3}{\mid}}{C}HCOOCH_3$ | 90 |
| 38 | 2-methyl-1-undecene | $C_9H_{19}C(CH_3)_2COOCH_3$ | 6 |
|    |                     | $C_9H_{19}C(CH_3)_2OCH_3$ | 14 |
| 39 | 4-methylstyrene | $4\text{-}CH_3C_6H_4\underset{\underset{CH_3}{\mid}}{C}HCOOCH_3$ | 50 |
|    |                 | $4\text{-}CH_3C_6H_4\underset{\underset{CH_3}{\mid}}{C}HOCH_3$ | 50 |
|    |                 |   | 50 |

We claim:

1. A process for the production from an olefinically unsaturated hydrocarbon of a branched-chain saturated carboxylic acid ester and/or the corresponding carboxylic acid wherein the number of ester or carboxylic acid groups is equal to the number of olefinic double bonds in the olefinically unsaturated hydrocarbon which process comprises reacting the olefinically unsaturated hydrocarbon with carbon monoxide and either alcohol or water respectively in the presence of oxygen, of an added protonic acid selected from the group consisting of hydrochloric acid, sulphuric acid and an organic acid, and as catalyst (a) palladium, and (b) copper, the component (a) being in the form of an elemental metal or a compound thereof, and the component (b) being in the form of a compound thereof.

2. A process according to claim 1 wherein the alcohol has the formula $R_2CHOH$ wherein R is independently hydrogen, alkyl, aryl or hydroxalkyl, or the two groups R together form a ring.

3. A process according to claim 1 wherein the olefinically unsaturated hydrocarbon is reacted with carbon monoxide and water, provided that the amount of water is less than 8 mole equivalents based on the olefinically unsaturated hydrocarbon, in the presence of a solvent other than an alcohol and the product produced thereby is the carboxylic acid.

4. A process according to claim 3 wherein the solvent is an ether.

5. A process according to claim 1 wherein the reaction is carried out at a temperature in the range 20° to 150° C.

6. A process for the production of an unsaturated carboxylic acid di-ester and/or the corresponding di-carboxylic acid which process comprises reacting an acetylenically unsaturated hydrocarbon with carbon monoxide and either alcohol or water respectively in the presence of oxygen, a protonic acid selected from the group consisting of hydrochloric acid, sulphuric acid, and an organic acid, and as catalyst (a) palladium, and (b) copper, the component (a) being in the form of elemental metal or a compound thereof, and the component (b) being in the form of a compound thereof.

7. A process according to claim 6 wherein the alcohol has the formula $R_2CHOH$ wherein R is independently hydrogen, alkyl, aryl or hydroxalkyl, or the two groups R together form a ring.

8. A process according to claim 6 wherein the acetylenically unsaturated hydrocarbon is reacted with carbon monoxide and water, provided that the amount of water is less than 8 mole equivalents based on the acetylenically unsaturated hydrocarbon, in the presence of a solvent other than an alcohol and the product produced thereby is the carboxylic acid.

9. A process according to claim 8 wherein the solvent is an ether.

10. A process according to claim 6 wherein the reaction is carried out at a temperature in the range 20° to 150° C.

11. A process for the production, from an acyclic olefinically unsaturated hydrocarbon of 2 carbon atoms, of a saturated carboxylic acid ester and/or the corresponding carboxylic acid wherein the number of ester or carboxylic acid groups is equal to the number of olefinic double bonds in the olefinically unsaturated hydrocarbon which process comprises reacting the acyclic olefinically unsaturated hydrocarbon of 2 carbon atoms with carbon monoxide and either alcohol or water respectively in the presence of oxygen, of an added protonic acid selected from the group consisting of hydrochloric acid, sulphuric acid and an organic acid, as catalyst (a) palladium, and (b) copper, the component (a) being in the form of an elemental metal or a compound thereof, and the component (b) being in the form of a compound thereof.

* * * * *